(12) United States Patent
Markoulides

(10) Patent No.: US 8,298,566 B2
(45) Date of Patent: Oct. 30, 2012

(54) PREPARATION OF BONE MATERIAL

(76) Inventor: Dimitrios Markoulides, Benoni (ZA)

( * ) Notice: Subject to any disclaimer, the term of this patent is extended or adjusted under 35 U.S.C. 154(b) by 1120 days.

(21) Appl. No.: 12/090,944

(22) PCT Filed: Oct. 19, 2006

(86) PCT No.: PCT/IB2006/002924
§ 371 (c)(1),
(2), (4) Date: Apr. 21, 2008

(87) PCT Pub. No.: WO2007/045977
PCT Pub. Date: Apr. 26, 2007

(65) Prior Publication Data
US 2008/0299175 A1  Dec. 4, 2008

(30) Foreign Application Priority Data

Oct. 19, 2005 (GB) .................................. 0521261.8

(51) Int. Cl.
A61F 2/00 (2006.01)
C08L 89/04 (2006.01)
C09D 189/04 (2006.01)
C09J 189/04 (2006.01)
A61L 24/00 (2006.01)

(52) U.S. Cl. ..................... 424/423; 106/124.7; 523/113; 523/115

(58) Field of Classification Search ........................ None
See application file for complete search history.

(56) References Cited

U.S. PATENT DOCUMENTS

| 2,968,593 | A  |    | 1/1961  | Evanston |
|-----------|----|----|---------|----------|
| 5,167,961 | A  |    | 12/1992 | Lussi et al. |
| 6,261,586 | B1 |    | 7/2001  | McKay |
| 6,689,375 | B1 | *  | 2/2004  | Wahlig et al. .................. 424/426 |
| 2003/0195629 | A1 | * | 10/2003 | Pafford et al. ............. 623/17.16 |
| 2005/0158535 | A1 | * | 7/2005  | Zhang et al. ................ 428/304.4 |
| 2006/0020266 | A1 | * | 1/2006  | Cooper ............................ 606/77 |

FOREIGN PATENT DOCUMENTS

WO      01/34216  A1   5/2001
WO    2004067052  A1   8/2004

OTHER PUBLICATIONS

Rodrigues et al., Biomaterials, vol. 24, Issue 27, Dec. 2003, pp. 4987-4997.*
Ramay et al., Biomaterials, vol. 25, 2004, pp. 5171-5180.*
Matsumoto et al., Hydroxyapatite Particles as a Controlled Release Carrier of Protein, Aug. 2004, Biomaterials, vol. 25, No. 17, pp. 3807-3812.
Habibovic et al., 3D Microenvironment as Essential Element for Osteoinduction by Biomaterials, Jun. 2005, Biomaterials, vol. 26, No. 17, pp. 3565-3575.

Markovic et al., Preparation and Comprehensive Characterization of Calcium Hydroxyapatite Reference Material, Nov.-Dec. 2004, Journal of Research of the National Institute of Standards and Technology(NIST), vol. 109, No. 6, pp. 553-568.
Friess, Collagen: Biomaterial for Drug Delivery, May 1998, European Journal Pharmaceutics and Biopharmaceutics, 1998, vol. 45, pp. 113-136.
Lynn et al., Antigenicity and Immunogenicity of Collagen, Nov. 2004, Journal of Biomedical Materials Research: Part B, vol. 71, No. 2, pp. 343-354.
Skinner et al., Preparation of the Mineral Phase of Bone Using Ethylenediamine Extraction, 1972, Calcified Tissue Research, vol. 10, No. 1, pp. 257-268.
LeGeros et al., Biphasic Calcium Phosphate Bioceramics: Preparation, Properties and Applications, Mar. 2003, Journal of Materials Science in Medicine, vol. 14, No. 3, pp. 201-209.
Thamaraiselvi et al., Biological Evaluation of Bioceramic Materials: A Review, Jul. 2004, Trends in Biomaterials and Artificial Organs, vol. 18, No. 1, pp. 9-17.
Temenoff et al., Injectable Biodegradable Materials for Orthopedic Tissue Engineering, Dec. 2000, Biomaterials, vol. 21, No. 23, pp. 2405-2412.
Roach, Why Does Bone Matrix Contain Non-Collagenous Proteins? The Possible Roles of Osteocalcin, Osteonectin, Osteopontin and Bone Sialoprotein in Bone Mineralisation and Resorption, Jun. 1994, Cell Biology International, vol. 18, No. 6, pp. 617-628.
Lopez-Lacomba et al., Use of rhBMP-2 Activated Chitosan Films to Improve Osseointegration, Mar. 2006, Biomacromolecules, vol. 7, No. 3, pp. 792-798.
Byler et al., Examination of the Secondary Structure of Proteins by Deconvolved FTIR Spectra, Mar. 1986, Biopolymers, vol. 25, No. 3, pp. 469-487.
Sachlos et al., Collagen Scaffolds Reinforced with Biomimetic Composite Nano-Sized Carbonate-Substituted Hydroxyapatite Crystals and Shaped by Rapid Prototyping to Contain Internal Microchannels, Sep. 2006, Tissue Engineering, vol. 12, No. 9, pp. 2479-2487.
Shi et al., Thermal Behavior of Dental Enamel and Geologic Apatite: An Infrared Spectroscopic Study, Nov.-Dec. 2003, American Mineralogist, vol. 88, No. 2, pp. 1866-1871.
Raynaud et al., Calcium Phosphate Apatites with Variable Ca/P Atomic Ratio II: Calcination and Sintering, Feb. 15, 2002, Biomaterials, vol. 23, No. 4, pp. 1073-1080.
Gao et al., Effects of Sintering Temperature on Structure and MC3T3-E1 Affinity of HA Derived from Natural Bone, 2004, Transactions of the 7th World Biomaterials Congress. p. 1451.
International Search Report for PCT/IB2006/002924, pp. 1-5, Mar. 2007.
German, Sintering Theory and Practice, Jan. 1996, Chapter 2: Solid State Sintering Fundamentals, ISBN: 978-0-471-05786-4, pp. 79-83.
Ripamonti et al., Sintered Porous Hydroxyapatites with Intrinsic Osteoinductive Activity: Geometric Induction of Bone Formation, Aug. 1999, South African Journal of Science, vol. 95, pp. 335-343.

* cited by examiner

*Primary Examiner* — Chris R Tate
*Assistant Examiner* — Douglas F White
(74) *Attorney, Agent, or Firm* — Brooks Kushman P.C.

(57) ABSTRACT

The invention provides a bone material having a specific surface area of at least 80 m$^2$/g and a protein content of less than 1800 ppm.

6 Claims, 7 Drawing Sheets

PREPARATION OF BONE MATERIAL

BACKGROUND OF THE INVENTION

This invention relates to the preparation of bone material. In particular, this invention relates to the preparation of single phase high surface area bone material, biphasic bone material and a combination thereof.

Calcium hydroxyapatite (HA), $Ca_{10}(PO_4)_6(OH)_2$ is an important inorganic material in biology and chemistry. Biological apatites, which are the inorganic constituents of bone, tooth enamel and dentin, are typically very variable in their composition and morphology, and contain different impurities including $Mg^{2+}$, $K^+$, $Na^+$, $(CO_3)^{2-}$, $(HPO_4)^{2-}$, $Cl^-$ and $F^-$. In general, these impure biological apatites are designated as calcium deficient or non-stoichiometric apatites. (A stoichiometric apatite can be defined where the Ca/P ratio is 1.67 for calcium hydroxyapatite whereas a non stoichiometric apatite is one where the Ca/P ratio is below 1.67 (Markovic et al, J of Res of NIST, 2004).)

Sintered Hydroxyapatite (HA) materials have been traditionally implanted in compact or porous form as a solid material or granules and have performed satisfactorily in the repair of diseased or damaged muskoskeletal systems. With respect to bone integration of the porous hydroxyapatite implants containing an interconnecting system of pores, these implants perform well in forming an intimate connection with the host bone. However, the disadvantage of these materials is that they do not break down or resorb back into the body easily and hence this prolongs the healing period.

On the other extreme, tricalcium phosphates (TCP) resorb or break down in the body easier. This desirable feature is negated by the fact that resorption or breakdown takes place faster than the rate of new bone formation, and hence creates voids which are not filled by bone but rather by connecting tissue. This creates poor mechanical stability at the implant site. In light of the two extremes described, biphasic calcium phosphate (BCP) materials were developed in the early 80's comprising hydroxyapatite (HA) and β-tricalcium phosphate derived from both synthetic materials and natural bone mineral. In contrast to the single phase HA's which have a very high surface area in its natural form, the BCP materials have very low surface area and coarse grains (due to high temperature processing parameters) which is not conducive for cellular activity during bone regeneration as large grains do not promote osteoblastic formation.

In maximizing bone regeneration and wound healing, both bioresorption (which is the rate that a device is resorbed or degraded in vivo) and bioactivity (which is potential of a device to contribute towards bone regeneration) need to be optimized. These factors are in turn dependent on the physical, chemical and biological state of the bioceramic as well as the intended application of the material. The chemical state refers to the purity and phase composition (i.e. the type of phase present in the device, being either highly resorbable or stable) of the bioceramic, whereas physical state would be the external surface area of the HA crystals, degree of micro/macro porosity and interconnectivity. The biological state of the material would be impacted by both chemical and physical factors as well as its source of origin, being either natural or synthetic. The presence of non collagenous proteins in the extracellular matrix of natural bone mineral, for instance, will impact on the biological state. Further, the degree of micro (diameter<10 μm) and macro porosity (diameter>100 μm) stemming from the trabeculae size, impact on the biological state as specific geometric configurations of pores in the material have been reported to have the unique capacity to bind specific bone morphogenic proteins (BMP), that make it possible to initiate the emergence of the osteogenic phenotype and/or the morphogenesis of bone. Altering the chemical state can have a negative impact on the physical state and vice versa this may not be the optimum model to maximize bioresorption and bioactivity.

In the quest to develop the most robust bioceramic device derived from natural bone mineral, the designer experiences that optimization of the one variable occurs at the expense of the other and this is typical of a technical contradiction. Some of the technical contradictions can be outlined as follows:

Reducing the thermal treatments so as to maximize the surface area (bioactivity) of the device, but without impacting on the purity, crystallinity and ultimately the immunogenic response of the implant.

Altering the phase composition of the device by incorporating a more resorbable phase (thereby increasing bioresorption) whilst not impacting negatively on the surface area and porosity.

Improving the osteoconduction (which is the ability of a device to provide the appropriate scaffold which would allow for cellular infiltration, attachment and calcified tissue deposition) by not limiting the osteoinductive potential (which is the ability of the device to stimulate a cascade of events that drives the emergence of osteogenic phenotype and the morphogenesis of bone) by altering the geometric configurations of the pores.

In summary, the ideal implant design would require robustness in altering the degree of resorption for various applications, whilst not impacting negatively on the bioactivity or drug delivery potential of the device.

An objective of the present invention is to provide a bioceramic offering the advantages of a high surface area hydroxyapatite component and a low surface area biphasic calcium phosphate (HA/βTCP) component. Both should be derived from natural bone mineral and have substantially the same geometric configurations as natural bone, with the purpose to regulate the degree of resorption whilst not impacting the bioactivity or drug delivery potential of the device. Further it is the objective of this invention for the attributes and the processes employed in producing high surface area hydroxyapatite component and the low surface area biphasic calcium phosphate to be superior over that descried in the prior art.

DETAILED DESCRIPTION OF THE INVENTION

According to a first aspect of the present invention there is provided a sintered hydroxyapatite material derived from natural bone material, the hydroxyapatite material having a specific surface area greater than 80 m²/gram and a protein content of greater than 150 ppm. In this description, the term 'specific surface area' is intended to mean surface area normalised by weight and all references to 'surface area' are references to 'specific surface area'. The term 'high surface area' is intended to mean a specific surface area greater than 80 m²/gram.

The specific surface area is preferably greater than 90 m²/gram, more preferably greater than 100 m²/gram, more preferably greater than 110 m²/gram, most preferably greater than 120 m²/gram.

The protein content is preferably greater than 175 ppm, more preferably greater than 200 ppm, more preferably greater than 250 ppm, more preferably greater than 300 ppm, more preferably greater than 350 ppm, more preferably greater than 400 ppm, more preferably greater than 450 ppm, more preferably greater than 500 ppm, more preferably greater than 550 ppm, most preferably greater than 600 ppm.

The protein content is preferably less than 1800 ppm, more preferably less than 1700 ppm, more preferably less than 1600 ppm, more preferably less than 1500 ppm, more preferably less than 1400 ppm, more preferably less than 1300 ppm, more preferably less than 1200 ppm, more preferably less than 1100 ppm, more preferably less than 1000 ppm, more preferably less than 900 ppm, more preferably less than 800 ppm, most preferably less than 700 ppm.

Preferably the hydroxyapatite material exhibits amide I and amide II peaks in a FTIR (Fourier Transform Infra Red) trace. (Without being limited by theory, the presence of these peaks is believed to be associated with the secondary structure of the residual protein in the material.)

Preferably the inorganic content of the material is characterized by the presence of OH peaks and/or carbonate ($CO_3$) peaks in the FTIR trace.

This material (high surface area hydroxyapatite material) comprises sintered hydroxyapatite material having a specific surface area of at least 80 $m^2/g$ and a protein content less than 1800 ppm, the material derived from natural bone mineral. The said protein content is characterized in the secondary structure by the Amide I and Amide II bands (Example 4). The hydroxyapatite material preferably does not illicit an immunogenic response when implanted in mammals (Example 2). The inorganic content of the material is further being characterized by the presence of OH and/or carbonate ($CO_3$) groups (See Example 4).

The prior art has focused in eliminating as effectively as possible all protein content in sintered bone material as it was believed that the presence of any protein or organic material would illicit an immunogenic response. Collagen until the early 50's was largely considered to be non immunogenic and is still considered to be a week antigen (Fries W, Eur Jour Pharmaceu Bio Pharmaceut 1998:45 113-136). Collagen however only comprises 85 to 90% of the protein in bone. The balance of the protein content is made of antigenic non collagenous proteins (NCP's) found in the extracellular matrix or connective tissues. These non collagenous proteins (NCP's) have been shown to play an important part in bone mineralization and some even have a role in binding the mineral and collagen together. The NCP's have been categorized by various techniques including FTIR Spectroscopy and are typically indicated by Amide I and Amide II bands. It has surprisingly been found that the presence of these NCP's does not necessarily illicit an immunogenic response, but depends strongly on the decellularization or deproteination process employed. Hence, the residual protein content of deproteinated xenograft implant does not necessarily correlate to immunogenicity. The effect the deproteinisation process has in eliminating NCP impurities as well as the impact it has in disorganizing the collagen triple helical structure will bear a major impact with regards to an antibody response (Lynn A. K J Biomed. Materials Res Part B pp 343-351).

According to a second aspect to the present invention there is provided a process for the preparation of the hydroxyapatite material from natural bone material comprising the steps of:
i) degreasing the bone material;
ii) deproteinising organic material present on the bone material;
iii) washing the bone material in an alcohol or a water soluble solvent having a boiling point not exceeding 70° C.;
iv) oxidising the bone material; and
vi) sintering the bone material.

Various methods of producing bone materials for medical uses are known in the art. The most common method of purifying bone mineral is to initially remove the fat and then heat the defatted bone mineral in a primary amine solution, most commonly being ethylene diamine, to solubulise the collagen and eliminate the presence of any protein. The earliest methods did not involve water washing which meant that the solubulized remnants were not effectively removed. Hot water washing was later introduced and a patent was granted to Armour & Co in 1961 (U.S. Pat. No. 2,968,593). However, the recommended washing with hot water after extraction resulted in undesirable crystal growth as reported by Skinner, Kempur and Pak: Calf Tiss. Res 10 (1972). Lussi et al U.S. Pat. No. 5,167,961 (1992) proposed washing with water below 60° C. to prevent crystal growth. This treatment of heating in a primary amine solution and repeatedly utilizing washing steps with water below 60° C. produced a bone mineral with protein content less than 135 ppm protein and an organic content less than 150 ppm. This document taught the necessity for reducing the protein content to these low levels to prevent the likelihood of immunogenic response taking place during implantation.

The main function of the ethylene diamine was to solubulise the collagen matrix and the water washing to wash away any solubulised collagen remnants. The boiling of the bone mineral in the ethylene diamine solution was typically for 50 hours as reported in U.S. Pat. No. 5,167,961. This long boiling period would ensure complete solubulisation of the collagen but would also result in the adsorption of degraded products on the surface of the bone mineral. Adsorption can be defined as the physical process which occurs when a liquid or gas adheres to surfaces or pores of an adsorbent material, typically affected by the reaction time or in this case boiling time. Long boiling times would be counter productive since this would require long washing cycles (typically between 5 and 25 days) for desorption to take place and long sintering times (typically 20 hours at 350° C.) to oxidize the organic residues.

Based on the prior art, a need exists to produce a bone material with an organic matter level which does not engender an immunogenic response when included in a mammal and yet which is capable of improved manufacture over the techniques taught in the prior art. In addition, a need exists for a bone material having an optimized specific surface area which bone material does not engender an immunogenic response when included in a mammal.

The improved process according to this second aspect to the present invention includes a more effective deproteinisation step with limited boiling in ethylene diamine to prevent adsorption of organic remnants coupled with a repeated oxidation step to minimize organic residues thereby eliminating the necessity for long sintering cycles.

The bone material may be degreased using chloroform as a solvent, preferably using Soxhlet fat extraction technique.

The organic material may be deproteinised according to this invention by contacting the bone material with a primary amine, preferably ethylene diamine. Alternatively, or in conjunction is the above, the bone material may be deproteinised by exposing the material to radiation, for example gamma radiation, preferably at about 15 KGy to 30 KGy dosages, including dosages of 20, 25 and 30 KGy.

The water soluble solvent is preferably methanol.

The step of oxidising the bone material may include washing the material with a peroxide solution, such as hydrogen peroxide solution and/or treating the material with ozone gas. Incorporation of ultraviolet light when washing with peroxide solution may be utilized.

The bone material may be sintered under ambient conditions. The bone material is preferably sintered in oxygen or air at a temperature of at least 200° C. to approximately 250° C., including temperatures of 210° C., 220° C., 230° C., and 240° C.

The bone material may further treated by at least one further oxidation treatment and/or sintering treatment. The further sintering treatment may take place at temperatures not exceeding 200° C.

The steps of oxidation and sintering treatment may be repeated to further reduce the protein content.

A final sintering treatment preferably does not exceed 250° C. and preferably does not exceed 2 hours. The total sintering time preferably does not exceed 8 hours in combination with the repeated oxidation treatments.

According to the present invention a high surface area bone material (hydroxyapatite medical device) that has a typical surface area of 100 $m^2/g$ is produced. Preferably the material is derived from bovine or porcine femurs. The process according to this invention provides a bone material with a protein content (<1800 ppm and >150 ppm typically) which is optimized by washing, repeated chemical oxidation and thermal sintering treatments. A combination of these treatments reduces the protein content and organic matter remaining after the initial deproteinisation step. Careful selection of the washing steps and sintering treatments is critical since this affects the purity and disturbs the crystal sizes of the natural apatite crystals thereby affecting specific surface area. Recrystallisation that takes place due to excessive thermal treatments may render the bone material unsuitable for use as a medical device, as the crystal size will not allow for osteoblastic adhesion which is critical for bone regeneration.

In the present invention following degreasing, the further treatment may be broken down into three steps. The first step removes the majority of the collagen from the bone material by gamma radiating the hydroxyapatite-collagen matrix, preferably at approximately 25 KGy dosage, followed by solubulising the collagen in boiling water for 2 hours and then repeatedly washing with a water soluble solvent in a Soxhlet device. The radiation of the bone material results in the scission of the collagen macromolecule which renders it soluble in water or water soluble solvent. This step can remove up to 75-85% of the total collagen in a total period of 5 hours.

The second step now involves heating with ethylene diamine to remove the balance of the collagen material from the bone. The fact that the majority of the collagen is now removed, results in weaker concentrations of ethylene diamine and shorter boiling times being utilized in solubulizing the residual collagen. The boiling in the ethylene diamine solution can now take place over a period of 5 hours. This period is short when compared to boiling times of prior art which have been reported to be in the order of 50 hours. This is in turn limits the amount of adsorption taking place on the surface of the hydroxyapatite surface during the boiling cycle and precludes the use of long washing cycles.

The third step involves washing with an alcohol based solvent such as methanol or other water soluble solvent after boiling step. Methanol has a lower boiling point than water and this can be used effectively in the Soxhlet apparatus to remove water soluble residues by repeat Soxhlet flushings without this treatment influencing crystal growth.

Further, the prior art has demonstrated the necessity of heating the bone material between 350 and 500° C. as a final and essential step in the oxidation of remaining organic residues which have not been removed during the washing step. In the present invention a combination of repeated chemical oxidation treatments and low temperature sintering treatments (not exceeding 250° C.) such steps being optionally being repeated to reduce protein content, yields a bone mineral with a specific surface area between 80 to 120 $m^2/g$. With a final sintering step at 250° C. for one hour, the product produced has typically a surface area of 100 $m^2/g$ as opposed to prior art bone material typically having a specific surface area of 60 $m^2/g$ (U.S. Pat. No. 5,167,961). Specific surface area is defined as the total external and internal area of a particle in relation to its weight. During sintering or thermal treatments there is a progressive loss of surface area, correlating to an increase in grain size. Hence, a higher surface area indicates that the natural apatite structure has not been affected adversely by the sintering treatments. Further a higher surface area is perceived to be more advantageous during the bone remodeling process as it assists in vascularization (i.e the ability to provide the wound site with oxygen and nutrients during the bone remodeling process).

Sintering of the bone material may be carried out by using microwave energy.

In summary, this aspect of the present invention describes a method for reducing processing times in the preparation of a hydroxyapatite material having a higher surface area and protein content when compared to the prior art. The method includes three steps comprising initially gamma radiating the bone material and solubulising the majority of the collagen matrix. The radiation treatment precludes long boiling treatments with ethylene diamine. This in turn precludes long washing times required to remove adsorbed constituents from the hydroxyapatite surface and reduces the boiling time down to 5 hours or less and the Soxhlet washing down to 2 days or less which is a vast improvement when compared to the teachings of the prior art which reports 50 hours for boiling and extensive washing of between 5 to 25 days. The repeated chemical oxidation steps after washing preclude prolonged sintering cycles (8 hrs or less vs. 20 hrs) at lower temperatures. This process results in hydroxyapatite material that has a high surface area and that is biocompatible when implanted in mammals (See Example 2 and FIGS. 2 & 3).

According to a third aspect of the present invention low surface area biphasic calcium phosphate bone material is provided comprising hydroxyapatite and tricalcium phosphate (TCP) derived from natural bone material and having a specific surface area less than 30 $m^2/g$. The term 'low surface area' is intended to mean the bone material produced by the second aspect of this invention and having a specific surface area less than 30 $m^2/g$.

The hydroxyapatite and tricalcium phosphate (TCP) derived from natural bone mineral preferably has a similar macro, micro and interconnected porosity as that of natural bone. The biphasic material is preferably comprised of an HA core surrounded by external TCP film. The TCP can be present in two forms either $\alpha$ or $\beta$-TCP, alone or in combination.

Prior art has shown that pure $\beta$-TCP and biphasic calcium phosphate (HA+$\beta$-TCP) is produced from biological apatites by transforming the calcium deficient HA's or non stoichiometric HA's to $\beta$-TCP via a sintering process. Depending on the calcium deficiency, sintering parameters and type of impurities present, various types of substitutions are possible in the calcium phosphate lattice. Hydrogen phosphate substitution $(HPO_4)^{2-}$ occurs typically above 700° C., whereas magnesium substitution ($Mg^{2+}$) typically occurs above 900° C. (LeGEROS R. Z. et al, J of Materials Science in Medicine, 14, 2003).

The transformation mechanism at these sintering temperatures involves Mg substitution of calcium and loss of $(CO_3)^{2-}$. The type of substitution that takes place during the sintering process affects the extent of the (β-TCP) transformation whereas the sintering temperature determines the formation of α or β-TCP.

As previously mentioned, the importance of the pore size for a bioceramic cannot be overemphasised as both the micro porosity (diameter<10 μm) which allows body fluid circulation and macro porosity (diameter>100 μm) which provides a scaffold for cell bone colonization, play a crucial role in osteoconduction. The pore volume of a bioceramic is directly correlated to the specific surface area with high surface areas corresponding to high pore volumes. As transformation of calcium deficient HA's occurs above 700° C., there is a substantial surface area loss due to shrinkage of the pores. Grain growth also occurs which results in the HA crystallites becoming fully stoichiometric and very stable thereby affecting resorbability (Thamaraiselvi et al. Trends Biomat. Artif Organs Vol 18 2004).

It is therefore advantageous to produce biphasic material at elevated sintering temperatures required for transformation to β-TCP, whilst simultaneously minimising the rate of pore shrinkage so as not to affect the porosity volume and the specific surface area of the biphasic implant. Further, the fact that HA resorbs slowly, while β-TCP degrades quicker, raises an issue with regards to the location and orientation of the TCP phases in the biphasic implant. Ideally, the β-TCP needs to be in contact with the biological fluids so as to increase the phosphate ionic product of the body fluid rather than the more stable HA. Hence, it is crucial that, in the initial stages of osteogenesis, the highly resorbable β-TCP layer surrounds the HA when positioned at the defect site.

The dominant sintering mechanism between 600 and 900° C. for calcium phosphate apatites is evaporation condensation controlled and is mainly influenced by the presence of vapour (Raynaud, S Biomaterials 23 (2002) pp 1073-1080). This suggests that vapour transport results in the repositioning of atoms along the surface eliminating the micropores, but not resulting in densification (German R M, Sintering Theory and Practice, Wiley Interscience 1996 pp 82-83). It is very common that for high surface area naturally occurring bone crystallites, sintering can be dominated by evaporation condensation across the pores, especially due to the presence of retained moisture in the material. Moisture has a high vapour pressure and as the sintering temperature increases, this aids vapour transport. Above 900° C., the dominant sintering mechanism changes to bulk mass transport across the grains which aids in densification and results in shrinkage (German R M, Sintering Theory and Practice, Wiley Interscience 1996, pp 79-80).

The current invention provides a biphasic material comprising of an HA core surrounded by a β-TCP skin, having essentially the same micro porosity and macro porosity as that of natural bone. Further a process is described for converting single phase hydroxyapatite bone material to biphasic material consisting of different proportions of hydroxyapatite (HA) and tricalcium phosphate (β-TCP) whilst suppressing the kinetics of surface area reduction and maintaining the micropores. The initial steps of defatting and deproteinisation of the bone mineral remain unchanged as described in the first aspect of the invention.

The sintering treatment according to this aspect to the present invention can be described in accordance with the following steps:
  sintering the hydroxyapatite material at an elevated temperature of between 500 and 1200° C.; and
  manipulating the vapour phase or sintering atmosphere in a cyclic fashion so as to dehydrate the external surface of the particles of bone material being treated.

The hydroxyapatite material may be sintered at an elevated temperature of over 500° C., preferably over 550° C., more preferably over 600° C., more preferably over 650° C., more preferably over 700° C., more preferably over 750° C., more preferably over 800° C. The hydroxyapatite material may be sintered at an elevated temperature of less than 1200° C., preferably less than 1150° C., more preferably less than 1100° C., more preferably less than 1050° C., most preferably less than 1000° C.

The vapour phase manipulation may involve heating the material with a gas mixture (dew point between −50° C. and −60° C., preferably −52° C.) to sintering temperature for approximately 20 minutes followed by a short vacuum cycle of approximately 10 minutes before reverting back to gas mixture treatment. This cycle may be repeated throughout the sintering treatment.

The effect of cyclic vapour phase manipulation as described is evident when comparing the specific surface area of such material to material sintered conventionally in air. The conventionally air sintered material results in a specific surface area of 4.5 $m^2/g$ when sintered at 800° C. for 3 hours. For the materials sintered utilising the cyclic vapour phase manipulation according to the present invention, at the same sintering temperature and time as described above, the specific surface area is 8.5 $m^2/g$. When comparing these values to the deproteinated bone mineral which had a specific surface area of 80 $m^2/g$ prior to sintering, the difference between the conventional and treated does not appear to be large. However, the effect of suppressing the evaporation condensation sintering mechanism is clearly evident on maintaining a larger volume of pores as the treated bioceramic sample (utilising the vapour manipulation technique) has approximately double (8.5 $m^2/g$ vs 4.5 $m^2/g$) the specific surface area when compared to the conventionally sintered material. This has a specific advantage for vascularization purposes when exposed to biological fluids.

The specific surface area loss ($\Delta S/So$) can be defined as the change in surface area divided by the original surface area prior to thermal treatment. The larger ($\Delta S/So$) becomes the greater the surface area loss during sintering. For the conventional sintered material ($\Delta S/So$) is 94.7% versus 90.0% for the sample utilising the vapour manipulation technique. Hence there is a 4.7% saving in surface area loss when incorporating the vapour phase manipulation technique at 800° C. for 3 hours. Depending on the sintering temperature and time when incorporating the vapour phase manipulation technique this saving in surface area loss can range from 2.5% through to 20%. A 20% saving is realized when vapour phase transport is fairly dominant.

The gas mixture will consist either of an oxygen/helium or a hydrogen/nitrogen mixture or a mixture of both so that the thermal conductivity of the mixture typically exceeds 60 mW/m.K at 525° C., more preferably 70 mW/m.K, more preferably 80 mW/m.K, more preferably 90 mW/m.K, most preferably 100 mW/m.K.

Dehydration of the external surface of the implant particles at temperatures greater than 500° C. and below 1200° C. creates a diffusion gradient of moisture in the crystals and converts the external area from hydroxyapatite to TCP. This is to prevent thermal gradients and allow for uniform heating of the highly porous material. This is essential as the cyclic vapour phase manipulation technique utilises vacuum which is a poor conductor of heat. The technique also switches to a highly thermal conductive gas mixture to balance thermal gradients throughout the material.

The effectiveness of the sintering atmosphere in maintaining a low dew point in combination with the sintering time will affect the proportion of TCP/HA produced On completion of the sintering treatment the material is cooled down in the presence of vacuum.

In the present invention, the external surface of natural bone material is converted to natural TCP with a cyclic (low dew point) vapour phase manipulation technique. The bone mineral trabeculae become the natural substrate with an external TCP formation on the external surface. Hence, natural bone material is converted to a biphasic material whilst still maintaining an open porous structure with the presence of trabeculae and interconnected porosity as is typical in natural bone. Typically an 85/15 (HA/β-TCP) material is produced at 800° C. when sintered for 3 hours, whereas, a 25/75 (HA/β-TCP) material is produced at 900° C. when sintered for 3 hours (see Example 3 & FIG. 5, FIG. 6).

In summary a biphasic material can be produced with different proportions of HA and TCP whose composition can be adapted for any surgical application. Most desirable is a biological decomposition period which is synchronized approximately with the bone regeneration rate, bearing in mind that the resorption of the TCP can be manipulated in terms of the teachings of the present invention. This results in bone replacement material, where the decomposition period can be adjusted to at least within certain limits during manufacture, thus stimulating accelerated bone formation without the implant material degrading too fast or too slowly.

According to a fifth aspect of the present invention, there is provided a medical device comprising sintered hydroxyapatite material derived from natural bone material, the hydroxyapatite material having a specific surface area greater than 80 $m^2$/gram, a protein content of greater than 150 ppm.

The invention extends to a biphasic medical device comprising sintered hydroxyapatite and tricalcium phosphate (TCP) material derived from natural bone material wherein the protein content is less than 1000 ppm, preferably less than 500 ppm.

According to a sixth aspect to the present invention there is provided a medical device comprising a combination of high surface area hydroxyapatite component and a low surface area biphasic calcium phosphate (HA/TCP) component.

Prior art has demonstrated the merit of implanting a mixture of a high surface area synthetic HA with a low surface area highly resorbable calcium sulfate component (U.S. Pat. No. 6,689,375). The ratio of the specific areas in combination with a highly resorable calcium sulphate component, yields a highly vascularized osteoconductive device but with a limited osteoinductive potential as the macropore formation in the matrix is dependent on the breakdown on the less resorbable component.

Besides macroporosity in excess of 100 μm providing an effective scaffold for bone cell colonization, the prior art also emphasizes the important role of pore configuration. The geometric pore configuration has been reported as having the unique capacity to give rise to a sequential cascade of events driving the emergence of the osteogenic phenotype and the morphogenesis of bone which impacts favourably on the osteoinductive potential of the device (Ripamonti et al S A Jour of Science 95, 1999). Hence the need arises to produce a multicomponent device that not only has good osteoconductive properties but also good osteoinductive capabilities.

The current invention proposes a multicomponent medical device, comprising of a high surface area hydroxyapatite component and a low surface area biphasic calcium phosphate (HA/βTCP) component, both derived from natural bone mineral and having substantially the same geometric configurations as that of natural bone. In this way the one component which has a high surface area yet stable matrix creates the basis for a highly a vascularized osteoconductive device (suitable for bone scaffolding) in combination with the low surface area biphasic calcium phosphate, that breaks down easily when in contact with biological fluids. This provides for a highly osteoconductive multicomponent medical device which still maintains the same geometric configurations as that of bone and which simultaneously does not impact on the osteoinductive or carrier potential of the device.

The components described that make up the multicomponent medical device can be mixed as powders or alternatively the one component could take the form of blocks and the other component as an injectable form. Cellulose based injectable carriers can be utilized such as the hydroxylpropylmethyl cellulose to form an injectable mass. Depending on the application, the multicomponent device can also take the form of a moldable mass. (See Example 5.)

It will be appreciated that the bone materials according to the present invention find useful application in several medical applications including the support and/or enhancement of bone formation and filling tooth cavities. Another application of the bone material (either together with the above or separately) is drug delivery.

The unique properties of these bone materials according to the present invention render the technology compatible with emerging technologies such as platelet rich plasma (PRP) and bone morphogenetic proteins (BMP's).

Platelet rich plasma (PRP) has been a breakthrough in the stimulation and acceleration of bone and soft tissue healing. It represents a relatively new technology that is part of the growing interest in tissue engineering and cellular therapy. Platelet rich plasma is derived from the patients blood using a cell separator or centrifuge which separates the PRP from the red blood cells. The PRP is then applied in a form of a gel or fibrin glue to the hydroxyapatite. Within PRP, the increased number of platelets delivers an increased number of growth factors to the surgical area. The seven known growth factors in PRP are: platelet derived growth factor aa (PDGFaa), PDGFbb, PDGFab, transforming growth factor-beta, (TGF-$b_1$), TGF-$b_2$, vascular endothelial growth factor (VEGF), and epithelial growth factor (EGF). These are native growth factors in their biologically determined ratios. This is what distinguishes PRP from recombinant growth factors. Recombinant growth factors are pure human growth factors, and are not native growth factors. Human cells such as platelets do not synthesize recombinant growth factors.

Some advantages of PRP:

Jump starts the cascade of osteogenesis in a bone graft,
Promotes early consolidation of the graft,
Improves trabecular bone density, and
Enhances osteoconduction.

Besides platelet derived growth factors other type of growth factors such as insulin type growth factors and epidermal type growth factors could also be utilized in conjunction with the high surface area and hydroxyapatite materials to speed up osteoconduction. Further, bone inductive proteins such as bone morphogenetic proteins (BMP 2 to BMP 14) as well as osteogenic proteins 1 and 2 (also known as BMP 7 & 8) which are known to induce bone can be utilized in conjunction with the high surface area and hydroxyapatite materials. The materials according to the present invention can be used as carriers of the BMP family members. Such modifications are deemed to be within the scope of this invention.

Besides β-TCP being highly resorbable calcium phosphate material and aiding mineralization, non collagenous proteins (NCP's) (which are found naturally in the extracellular matrix of bone) have also shown to play an important role in the initiation and a control of mineralization during de novo bone formation. Some of the most common NCP's are osteopontin, bone sialoproteins and osteocalcin. It has been suggested that osteocalcin acts as a chemo-attractant for osteoclasts, while bone sialoproteins and osteopontin facilitate the binding of osteoclasts (Roach, Cell Biology Int, Vol 18, 1994). The suitable NCP's can be isolated from the mineralized matrix and can be concentrated so as to be recombined with suitable delivery systems. This in turn can be utilized in conjunction with the multicomponent device as described in this invention.

It will be further appreciated that the bone materials according to the multicomponent device as hereinbefore described have limited application in load bearing applications when utilized in isolation in vivo. However, when utilized in conjunction with mechanical aids (such as spinal spacers and cages) and high strength biocompatible polymers, the multicomponent device can be used in load bearing applications in vivo. The spacers comprise load bearing members and are suitable for utilizing bone materials in load bearing applications such as spinal fusions (U.S. Pat. No. 6,261,586). The main function of a spacer is to maintain spaces between vertebrae of the spine while bone growth occurs. In this way, the load is diverted away from the implant until such time that the implant is replaced by host bone.

Photopolymerizable poly(anhydrides) with suitable strength have been utilised to fill bony defects and provide the necessary mechanical strength for use in orthopedics or load bearing applications. These polymers would also be suitable for the multicomponent device when used in load bearing applications. These polymers are injectable and can be polymerized in situ with 150 mW/cm$^2$ of blue light. These materials are polymers of sebacic acid (SA) alone, or copolymers of SA and 1,3-bis(p-carboxyphenoxy) propane (CPP), or 1,6-bis(p-carboxyphenoxy) hexane (CPH). Depending on the monomer(s) used, the mechanical properties as well as degradation time can be varied. In general, compressive strengths of 30-40 MPa and tensile strengths of 15-27 MPa are obtained which are similar to those of cancellous bone. Poly(sebacic acid) (PSA) degrades quickly (about 54 h in saline), whereas poly(1,6-bis(p-carboxyphenoxy)hexane (PCPH) degrades over a period of approximately 1 year. Therefore, combinations of different amounts of SA with CPH would result in a polymer with degradation properties custom-designed for a specific application depending on the bone regeneration rate of the host bone. These polymers are surface-eroding and therefore maintain the bulk mechanical properties while undergoing degradation (Temenoff et al, Biomaterials, Vol. 21 (23) (2000) pp. 2405-2412).

Further chitosan films used to cover prostheses comprising of a bioresorbable polymer of N-acetyl glucosamine and glucosamine have shown a good potential of acting as a carrier of rhBMP2(Locomba Lopez J. L. et al Biomacromolecules 7 (3) 792-798 2006.). The filmogenic properties and rapid degradation rates coupled with its ability for cellular growth and proliferation, make this film also potentially suitable for covering scaffolds and optimising the carrier potential of the device according to the present invention.

All modifications described herein including growth factors (PRP & BMP), non collagenous proteins, chitosan films, biodegradable polymers, mechanical aids such as spacers and their relationship to the current invention are deemed to be within the scope of this invention.

The invention will now be described with reference to the following non-limiting examples and Figures in which:

FIG. 1 demonstrates the percentage collagen remaining after repeated oxidation treatments in conjunction low temperature sintering treatments according to the present invention.

Figure 4:
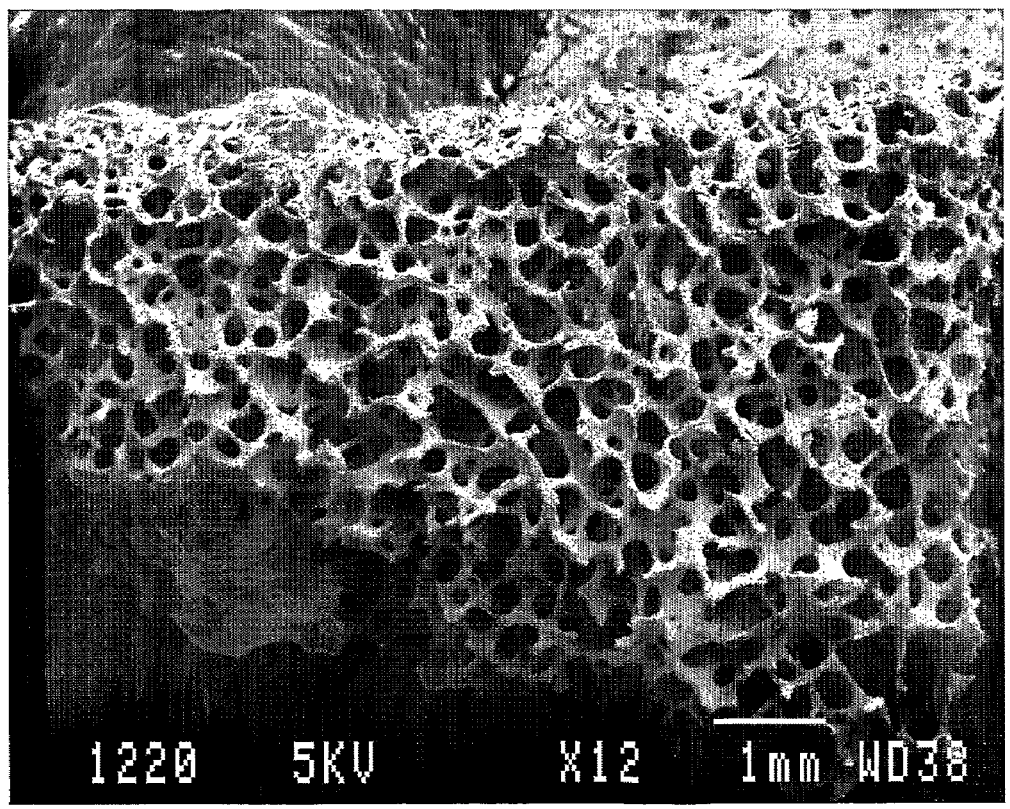

FIG. 4 demonstrates the shape and size of the trabeculae of the biphasic material according to the present invention.

Figure 5:
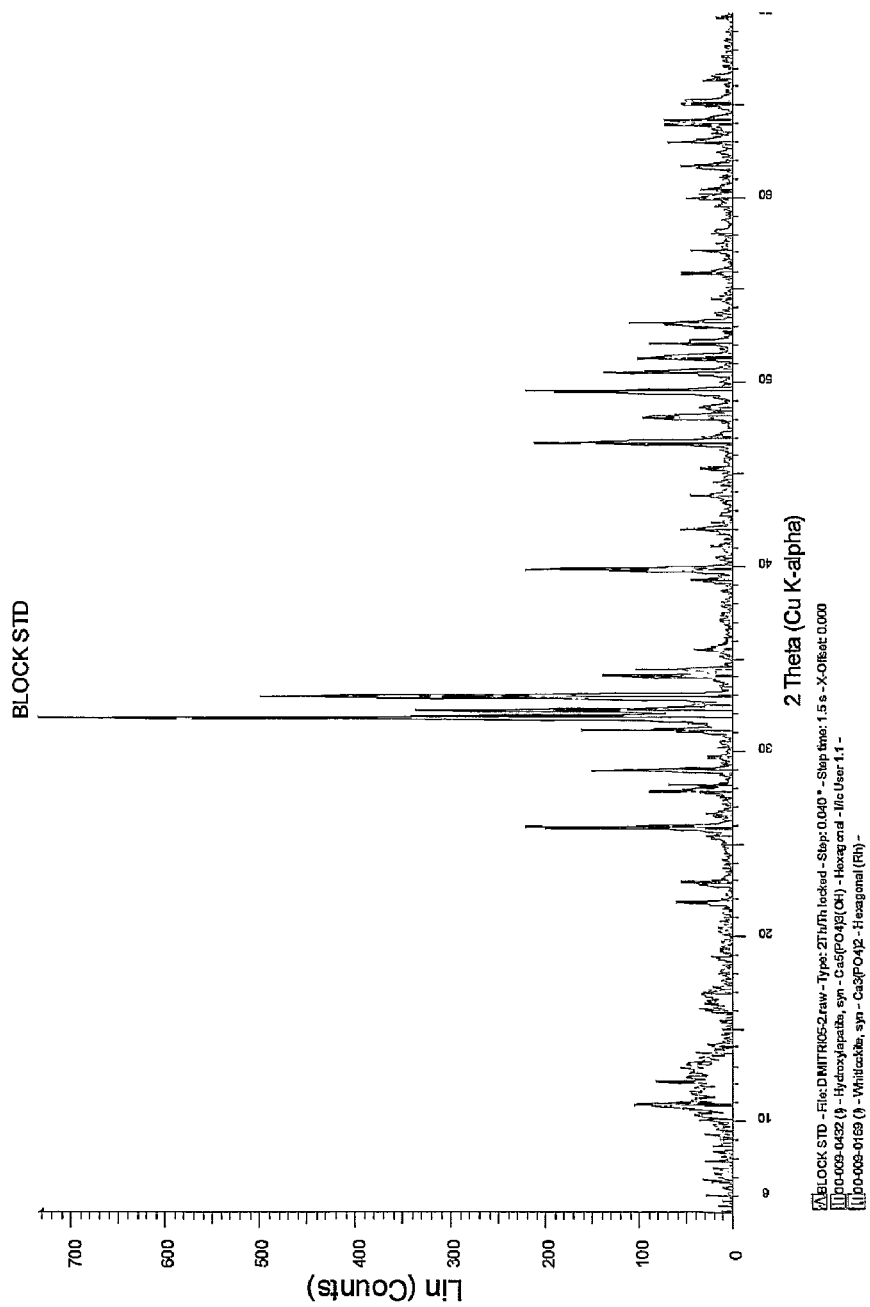

FIG. 5 shows the XRD spectra of the biphasic material demonstrating the HA and (β-TCP) Whitlockite peaks.

Figure 6:
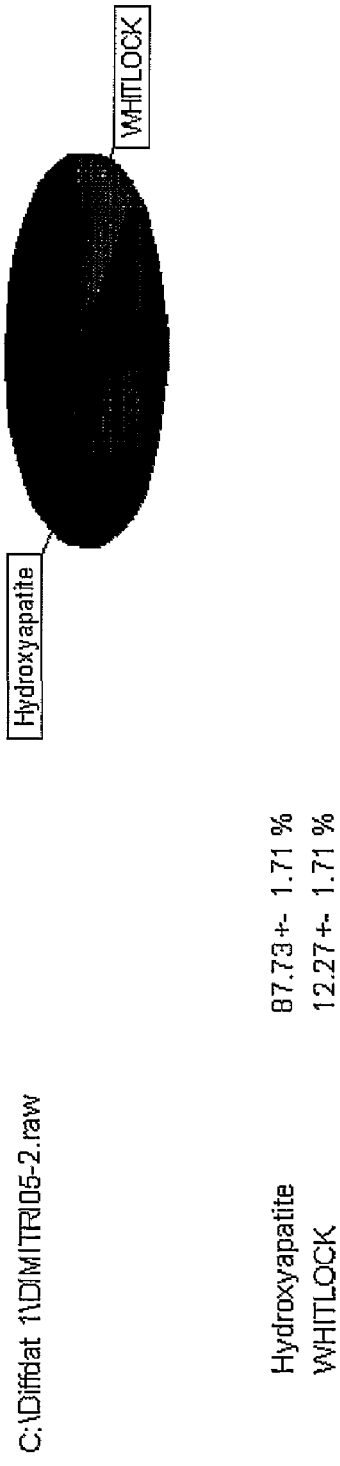

FIG. 6 shows the quantative analysis of the phase proportion for the biphasic material that was produced as per Example 3.

Figure 7:
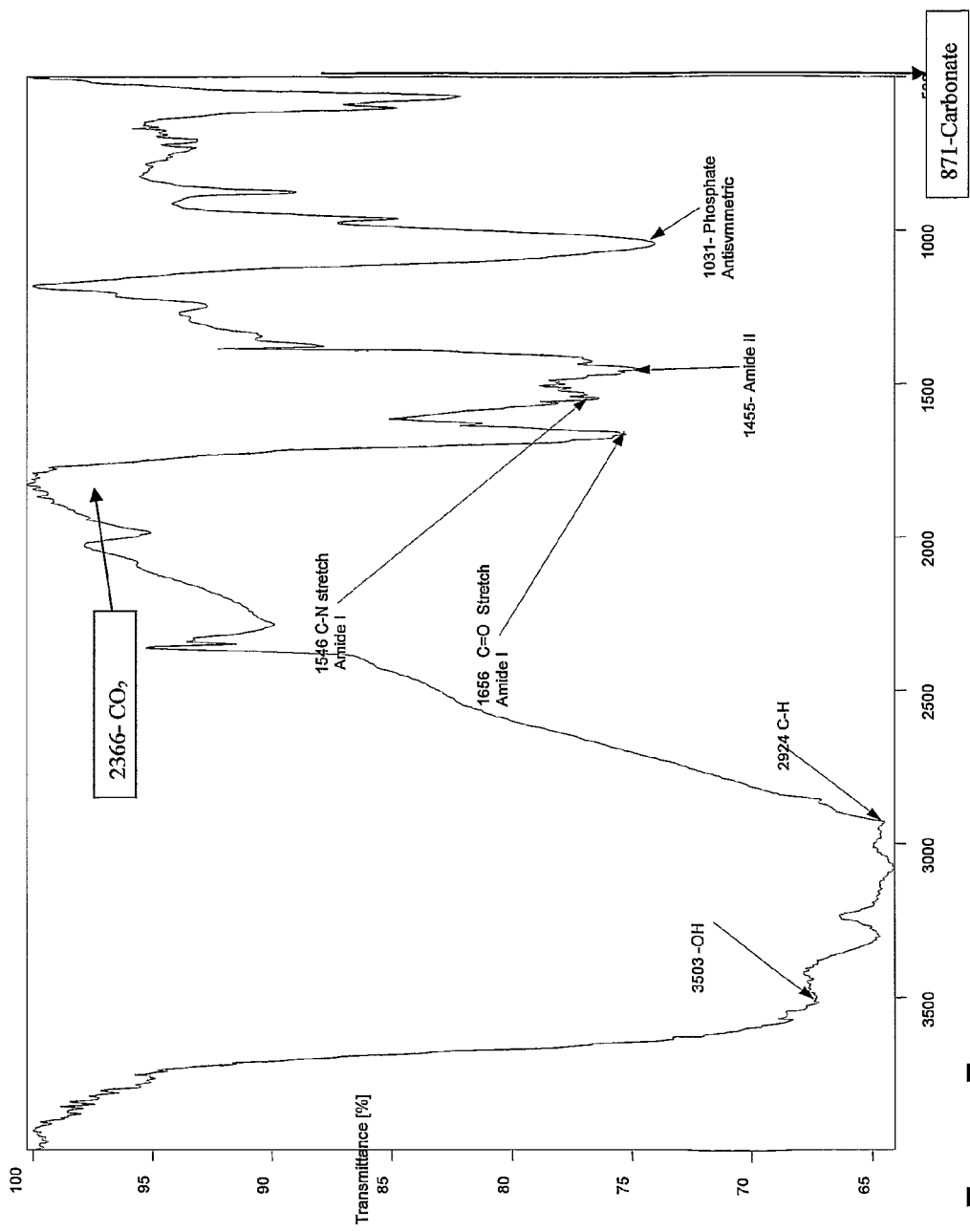

FIG. 7 shows the FTIR trace of defatted and unsintered bone mineral.

Figure 8:
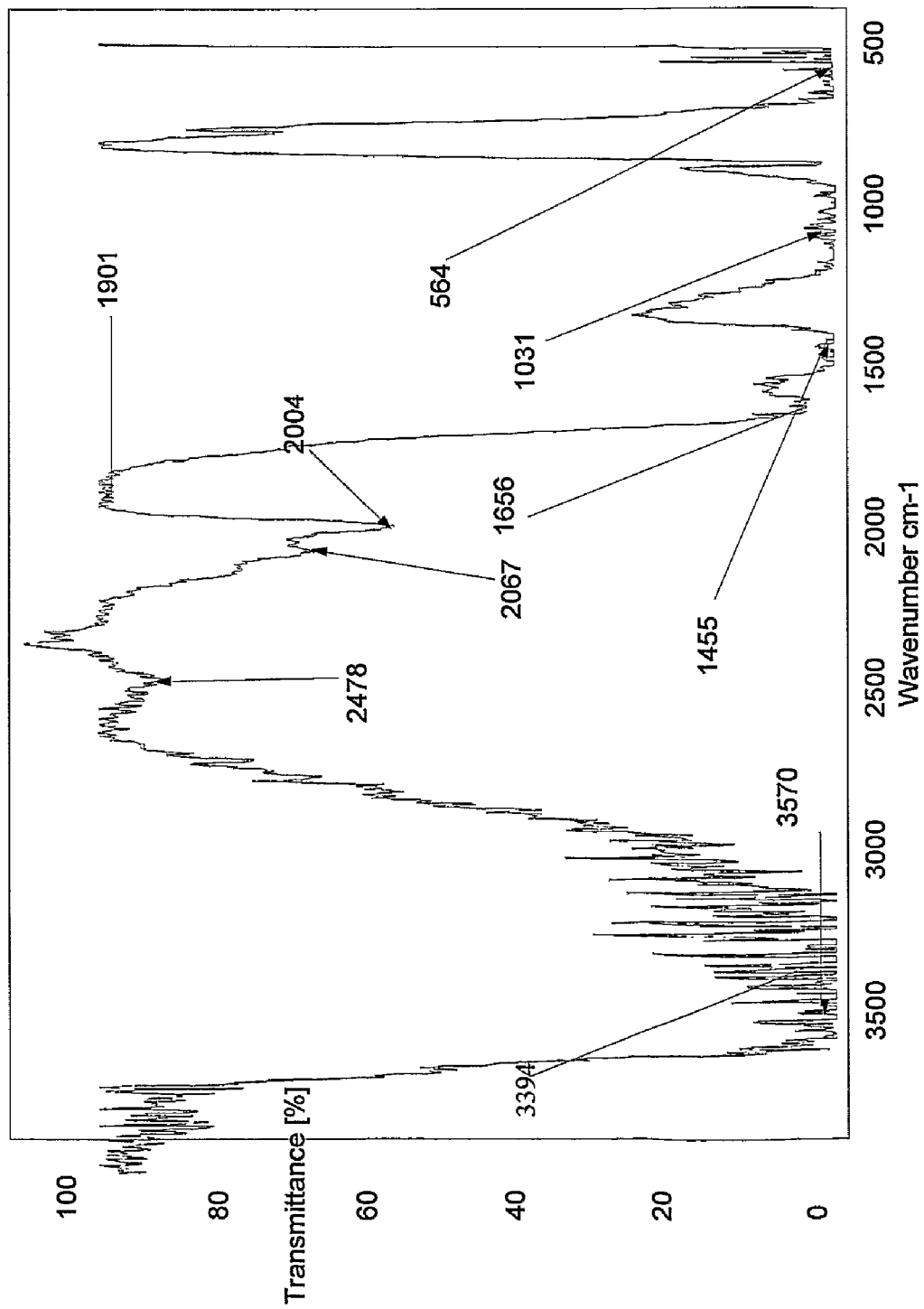

FIG. 8 shows series of FTIR of the high surface area hydroxyapatite material

Figure 9:
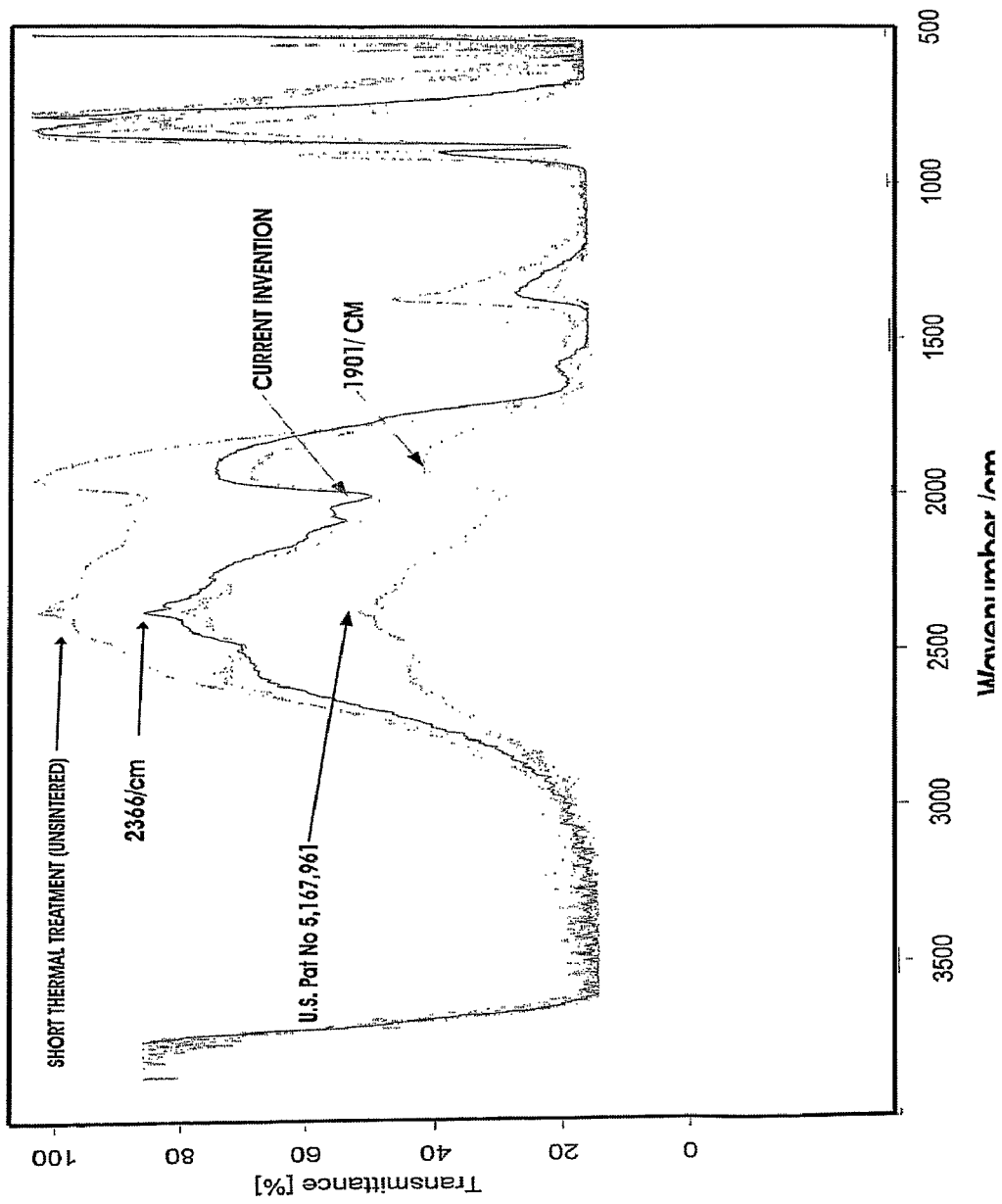

FIG. 9 semi quantitative FTIR demonstrating band intensity for different thermal treatments.

EXAMPLE 1

(a) Preparation of Defatted Bone

Bovine or porcine femurs are sliced and sawed into pieces 5 mm thick, which are initially cleaned by removal of soft tissues before being transferred to a Soxhlet Extractor whereby the fat is removed utilizing chloroform and extracting for 10 hours. The samples are then removed from the Soxhlet apparatus and dried overnight.

(b) Preparation utilizing Gamma Radiation in Deproteinization Step

The defatted bone is irradiated at 25 KGy, before boiling the samples in distilled water. The bone samples are then washed with methanol in the in the Soxhlet apparatus for 5 hours.

(c) Preparation utilizing Ethylene Diamine in Deproteinization Step

The defatted bone is then boiled in an azeotropic mixture of ethylene diamine with water. The material is boiled for a period of 5 hours before being decanted. The bone samples are then washed with methanol and placed in the Soxhlet apparatus before being washed with methanol for an additional 5 hours.

After drying the weight loss ranges between 35 to 43% depending on the pore size and crystal size of the bone material.

(d) Repeated Oxidation Treatment

The samples prepared are then washed with hydrogen peroxide solution and left overnight. Samples are then sintered in oxygen to 200° C. for one hour, before repeating the washing with hydrogen peroxide solution. Samples are treated until there is no visual evidence of light yellowish residues on the surface.

e) Final Sintering Treatment

Samples are then finally sintered at 250° C. for two hours depending on the strength of the compact that is required.

Figure 1:
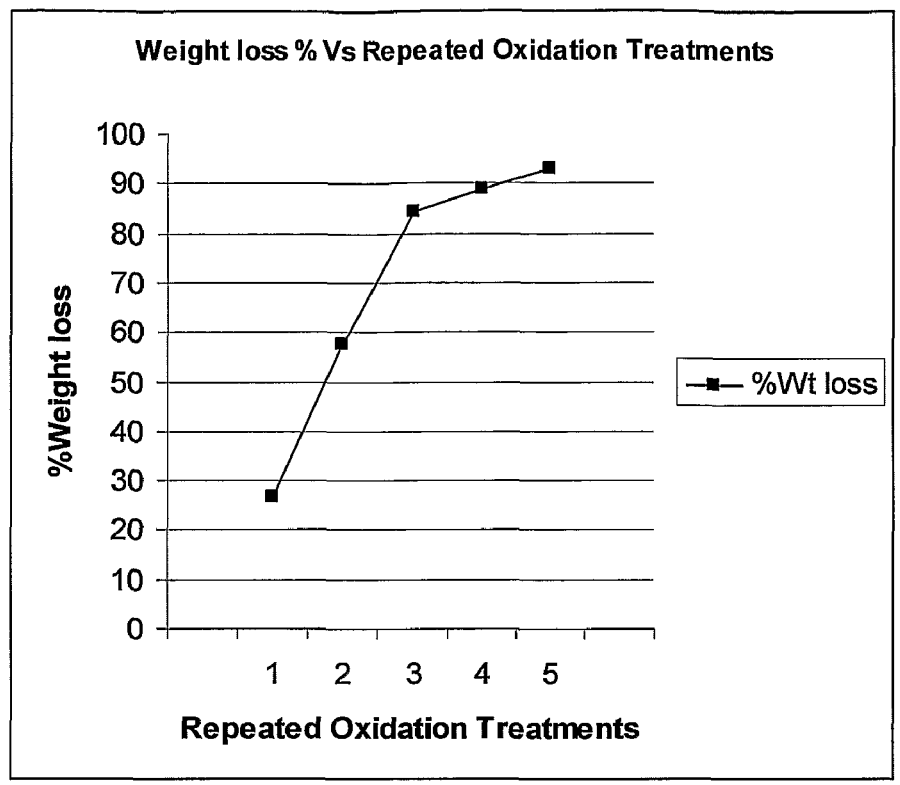
Figure 2:
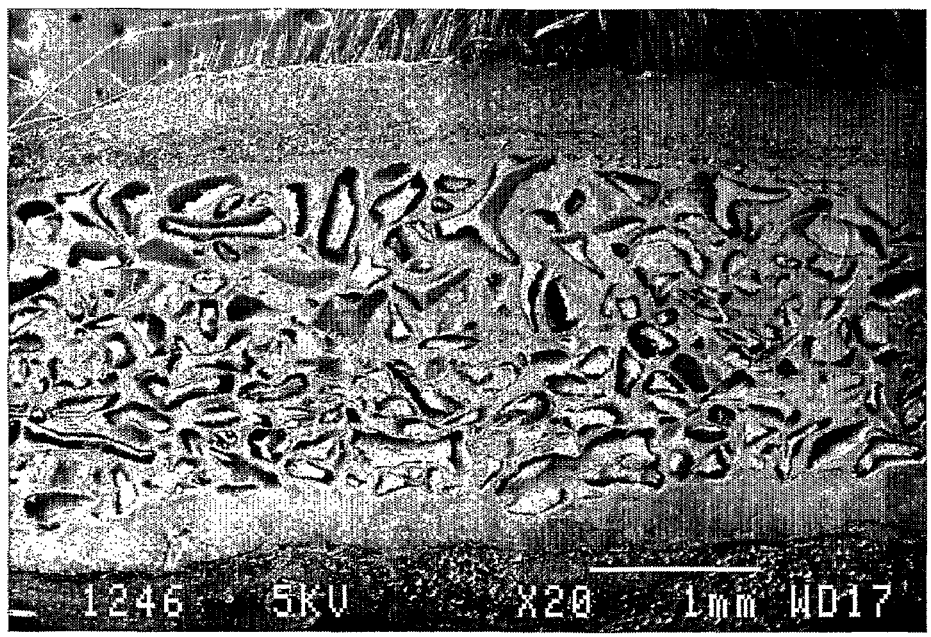
FIG. 2 shows an ESM image of tissue formation in implant trabeculae after 30 days of implantation as per Example 2.
Figure 3:
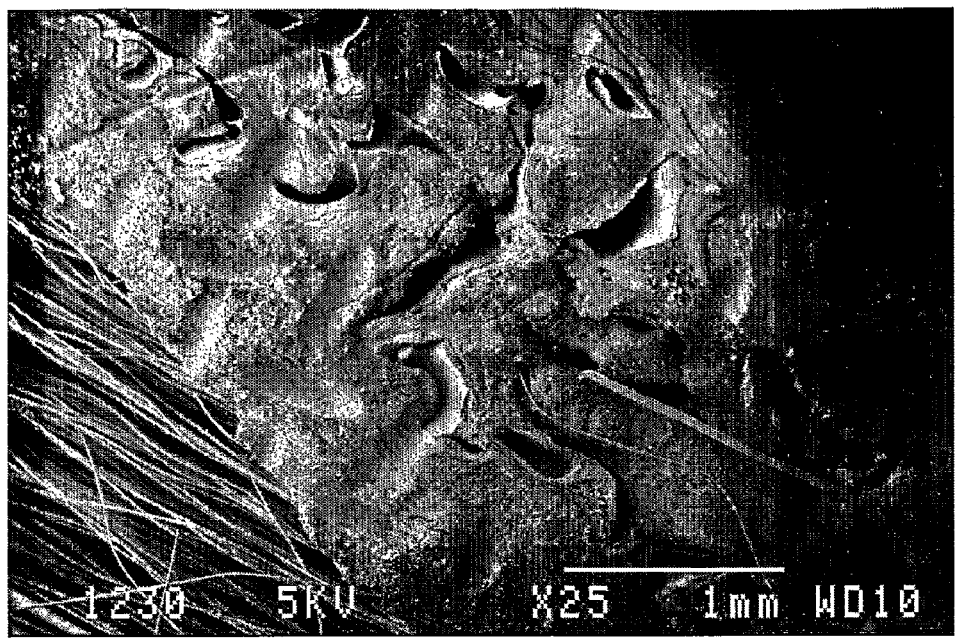
FIG. 3 shows an ESM image of tissue healing (tissue integration) in an implant after 90 days of implantation as per Example 2.

The weight loss (% wt) per repeated oxidation treatment is shown in FIG. 1.

EXAMPLE 2

The aim of the study was to evaluate the biocompatibility of the high surface area material hydroxyapatite materials produced according to the current invention that had a protein content of 1800 ppm in comparison to a control sample (Geistlich Biomaterials) whose protein content was reported to be <135 ppm as per U.S. Pat. No. 5,167,961. The protein analysis of the test sample was carried out on a LECO™ FP 2000 Protein analyzer. The objective of the exercise was to compare if there would be any differences with regards to tissue tolerance and integration for the two materials in question. Surgical subcutaneous pouches were created in 30 Wirstar rats so that the pouches would not be in contact with one another. 10×10×2 mm thick high surface area hydroxyapatite bone material samples were inserted on the ventral side as per ISO 10993 part 1. The animals were monitored over the next 90 days for presence of any discomfort. X-rays were taken at 30, 60 and 90 days to assess the tolerance and integration into the implanted sites of the test samples and the control samples. Table 1 summarises the specific surface areas for the test and control sample measured. Surface area analyses are performed on a NOVA 1000e Surface area and Pore Size Analyser, using nitrogen gas as an adsorbent.

TABLE 1

| Material | Specific Surface Area $m^2/g$ |
| --- | --- |
| Current Invention (Test) | 100 |
| US Pat No 5,167,961 (Control) | 75 |

The following histological assessments were carried out on both materials:

Extent of fibrosis and inflammation

Degeneration as determined by changes in tissue morphology

Number and distribution of inflammatory cell types as a function of distance from the implant tissue material The quality and quantity of tissue growth The data below in Table 2 & 3 reflects the severity of test and control samples for various conditions at 60, 90 days based on the morphological findings of subcutaneous implantations. Table 4 describes the total observations throughout the study.

TABLE 2

Severity of Biologic Response after 60 days

| | Group | Biologic Response after 60 Days | | | |
| --- | --- | --- | --- | --- | --- |
| | | Negative | Mild | Moderate | Severe |
| Encapsulation | Test | 8 | 4 | 2 | 0 |
| | Control | 1 | 10 | 2 | 0 |
| Inflamation | Test | 0 | 10 | 4 | 0 |
| | Control | 0 | 5 | 6 | 2 |
| Angiogenesis | Test | 0 | 1 | 13 | 0 |
| | Control | 0 | 0 | 12 | 1 |

TABLE 3

Severity of Biologic Response after 90 days

| | Group | Biologic Response after 90 Days | | | |
| --- | --- | --- | --- | --- | --- |
| | | Negative | Mild | Moderate | Severe |
| Encapsulation | Test | 3 | 10 | 1 | 0 |
| | Control | 2 | 11 | 0 | 0 |
| Inflammation | Test | 6 | 6 | 3 | 0 |
| | Control | 4 | 8 | 0 | 0 |
| Angiogenesis | Test | 1 | 10 | 4 | 0 |
| | Control | 0 | 11 | 1 | 0 |

TABLE 4

Severity of Biologic Response for Total Observation

| | Group | Biologic Response Total Observations | | | | |
| --- | --- | --- | --- | --- | --- | --- |
| | | Negative | Mild | Moderate | Severe | Total |
| Encapsulation | Test | 11 | 15 | 3 | 0 | 29 |
| | Control | 3 | 20 | 2 | 0 | 25 |
| Inflammation | Test | 6 | 16 | 7 | 0 | 29 |
| | Control | 4 | 13 | 6 | | 25 |
| Angiogenesis | Test | 1 | 11 | 17 | 0 | 29 |
| | Control | 0 | 11 | 13 | 1 | 25 |

The raw data was analyzed utilising contingency tables and two sample proportion testing. The statistical outputs for Tables 5, 6 and 7 are derived utilising Minitab statistical package.

TABLE 5

Statistical Outputs after 60 days with respect to various conditions (95% confidence).

| | Biologic Response after 60 Days | | |
| --- | --- | --- | --- |
| | P Value | Statistical Conclusion | Practical Conclusion |
| Encapsulation | 0.018 | Reject Ho | Significant Difference Between Test & Control |
| Inflammation | 0.183 | Fail To Reject Ho | No Significant Difference Between Test & Control |
| Angiogenesis | 0.241 | Fail To Reject Ho | No Significant Difference Between Test & Control |

TABLE 6

Statistical Outputs after 90 days with respect to various conditions (95% confidence).

| | Biologic Response after 90 Days | | |
| --- | --- | --- | --- |
| | P Value | Statistical Conclusion | Practical Conclusion |
| Encapsulation | 0.759 | Fail to Reject Ho | No Significant Difference Between Test & Control |
| Inflammation | 0.188 | Fail To Reject Ho | No Significant Difference Between Test & Control |
| Angiogenesis | 0.957 | Fail To Reject Ho | No Significant Difference Between Test & Control |

TABLE 7

Statistical Outputs for overall observations with
respect to various conditions (95% confidence).

Biologic Response for Total Observations

| | P Value | Statistical Conclusion | Practical Conclusion |
|---|---|---|---|
| Encapsulation | 0.074 | Fail To Reject Ho | No Significant Difference Between Test & Control |
| Inflammation | 0.953 | Fail To Reject Ho | No Significant Difference Between Test & Control |
| Angiogenesis | 0.634 | Fail To Reject Ho | No Significant Difference Between Test & Control |

Based on the statistical analysis (at a significance level of $\alpha=0.05$) data it can be stated that:

Encapsulation: There is no statistical difference between the test and control sample after 90 days of implantation (Table 6). The test samples show a significant reduced amount of encapsulation at 60 days (p value=0.018, Table 5) when compared to the control sites. Evaluating the observations across the whole study in total (57 observations); there is no statistical difference (p value=0.074) between control and test samples.

Inflammation: The mean proportion of mild and inflammatory responses is larger for the test sites (22/29=76%) in comparison to control (17/25=68%) for negative and mild inflammation Table 4. However there is no statistical difference between the test and control sample after 60 or 90 days of implantation (Tables 5 & 6). Studying the observations across the whole study in total (57 observations); there is no statistical difference (p value=0.953) between control and test samples. Based on the above, the higher level of protein content of the Test material does not result significantly in inflammation.

Angiogenesis: Even though the test material showed a higher mean proportion of moderate angiogenesis when compared to the control (17/29=58%) versus (13/25=52%) there is no significant difference. Hence, there does not appear to be any statistical difference between the test and control sample after 60 or 90 days of implantation (Tables 5 & 6). Studying the observations across the whole study in total (54 observations); there is no statistical difference between control, and test samples (p value.=0.634) The higher specific surface area of the test material does not show improved angiogenesis over the 90 day evaluation based on the current study period.

CONCLUSIONS

The higher level of protein content of the test material does not appear to significantly effect on the inflammatory response (p value=0.86).

The test material revealed a substantial reduction in the occurrence of encapsulation 57% for negative encapsulation versus 7.6% at 60 days when compared to the control (Table 5). Overall there was no significant difference between the test and control taking the samples at 90 days (p value=0.241).

Even though the test proportion for mild angiogenesis is greater (58%) than the control (50%), the test material does not show statistically improved angiogenesis over the 90 day evaluation based on the current sample size (p value=0.634).

Evaluating the observations across the whole study in total (57 observations), there is no statistical difference between control and test samples for encapsulation, inflammation and angiogenesis. The test sample was comparable in tolerance to the control samples even though the test samples had higher level of protein content. The test sample with the higher surface area did not show significant improvement with regards to angiogenesis for the study period. A larger sample size would be required to evaluate angiogenesis but this was beyond the scope of the study. Based on the results from this study comparing the means of the test to the control, the test samples means were lower for inflammation and encapsulation and were higher for angiogenesis even though there was no significant difference. In conclusion, the higher protein content of the test material, did not illicit an immunogenic response neither did it affect the biocompatibility or tissue tolerance to any significant effect.

EXAMPLE 3

A high surface area hydroxyapatite bone material according to the present invention was converted to a biphasic material consisting of hydroxyapatite (HA) and Tricalcium phosphate (TCP). The following procedure was followed in producing this material.

The hydroxyapatite material was heated to 800° C. in pure oxygen at a flow rate of 5 l/min and manipulation of the vapour phase or sintering atmosphere took place in a cyclic fashion so as to dehydrate the external surface of the particles. The vapour phase dew point was kept between −50 and −60° C. at sintering temperature for 20 minutes followed by a short vacuum cycle of 10 minutes before reverting back to gas mixture treatment. The total sintering cycle time was 3 hours and the flow rate was kept at 5 l/min. As the material is highly porous a gas mixture of oxygen/helium was utilised to increase the thermal conductivity of the gas in order to ensure even heating throughout the material. On completion of sintering, the samples were cooled under vacuum to prevent possible adsorption effects from the gases throughout the sintering treatment.

The biphasic bone device derived from a natural source comprises of an open porous structure with the presence of trabeculae and interconnected porosity as is typical in natural bone. The diameter of the trabecular size is typically from 200 μm to 500 μm, for example 250 μm (FIG. 4), which shows evidence of shrinkage when compared to the starting material that had a trabecular size typically of 500 μm.

EXAMPLE 4

A sample of defatted and unsintered bone mineral (FIG. 7) was compared to the sintered high surface area hydroxyapatite material (FIG. 8) by Fourier Transform Infrared Spectroscopy (FTIR) to evaluate the state of the inorganic materials and to evaluate the protein conformation of the proteinacious residue present in the material. The characteristic bands of the FTIR spectra (FIGS. 7 & 8) were identified and described as is shown in Table 8.

TABLE 8

Band Position of Test Material

| Band position | Current Invention | Band Identity |
|---|---|---|
| 472 | √ | Phosphate v1 |
| 564 | √ | Phosphate v4 |
| 603 | √ | Phosphate v4 antisymmetric |
| 873 | √ | Carbonate v2 |
| 962 | √ | Phosphate v1 symmetric |

TABLE 8-continued

Band Position of Test Material

| Band position | Current Invention | Band Identity |
| --- | --- | --- |
| 1031 | √ | Carbohydrate Ring Vibrations |
| 1455 | √ | Amide II |
| 1631 | √ | H—O—H Bending mode of water |
| 1656 | √ | C=O Stretch Amide I |
| 2366 | √ | $CO_2$ Band |
| 3420 | Absent | Dehydration of Collagen Fibrils |
| 3394 | √ | Amide A |
| 3570 | √ | OH -Groups |

From Table 8 the inorganic component of the test material can be summarized as follows. An apatite material consisting of:
OH-Groups,
Carbonate ions,
Phosphate ions,
Moisture in the matrix, and
$CO_2$.

The organic residue remaining from protein can be categorized by:
Amide I,
Amide II, and
Amide A.

The longer sintering times result in the dehydration of the collagen fibrils. This dehydration in turn destabilizes the triple helical structure of collagen and affects the secondary structure. The change in the secondary structure is directly correlated to the stretching vibrations of the C=O bond and can be correlated to the triple helical structure of collagen (Byler et al, Biopolymers 25, 1986). Caution should however be exercised as the Amide I band can be masked by the H—O—H band of moisture appearing in the lattice at 1631/cm.

The present invention on the other hand, has shorter thermal treatments and does not dehydrate the collagen residue fibrils to the same extent. With the presence of the Amide I band, the triple helix secondary structure of the collagenous residue is still intact after deproteinisation takes place.

In summary, the apatite material showing the presence of hydroxyl groups being characterized by 3570/cm (test material), can be considered to be hydroxyapatite consisting of carbonate hydrogen phosphate. During heating, the carbonate ions can substitute for hydroxide (Type A substitution) or phosphate (Type B substitution) (Sachlos et al, Tissue Engineering Vol 12 No 9, 2006).

EXAMPLE 5

Practical application of the multicomponent device for filling of small bone defects utilising two components in powder or granule form. The multicomponent device consists of two components:

Component 1: High surface area, single phase HA powder with surface area typically at 100 $m^2/g$; and
Component 2: Low surface area biphasic calcium phosphate comprising 80/20 (HA-β-TCP) with surface area typically in the regions of 8 $m^2/g$.

The ratio of component 1 to component 2 will depend on the clinical requirement. A larger proportion of component 1 will result in more bony contact whereas more of component 2 will increase the resorption rate. Typically a 70/30 ratio is used which can be prepared by weighing out the components and mixing with a spatula. The mixture can be mixed with the patient's blood or with saline solution and placed at the defect site.

For larger defects, component 1 is utilised in a form of a block, whilst component 2 is mixed with a 2% by weight bioresorbable cellulose based carrier gel that can be injected by means of a syringe uniformly throughout the block and defect site.

EXAMPLE 6

The objective of this exercise was to compare transmittance as a function of heating time. Four samples (one defatted but unsintered, 2 prepared by current invention and one supplied by Geistilch Biomaterials U.S. Pat. No. 5,167,961) were taken and ground by hand by means of an agate mortar. Special care was taken in weighing the samples to +/−0.05 mg with the balance having a resolution of 0.01 mg. All samples were mixed with 2.5% KBr and pelletized before analysis on the Bruker Tensor 27 FTIR spectrophotometer. The 500 to 4000/cm region was scanned. After scanning, a baseline correction was carried out so as to carry out a semi-quantitative analysis of the spectra bands present.

From the analysis as shown in FIG. 9, all samples showed the presence of strong bands at 2366 and 1994/cm. It is evident that the sample with little thermal treatment (unsintered sample) showed the highest peak whereas the sample with the longest treatment (U.S. Pat. No. 5,167,961) showed the lowest peak. The peak near 2366 is representative of $CO_2$ absorption retained in the hydroxyapatite structure due to thermal decomposition of the carbonate ions (Shi et al, American Mineralogist Vol 88, pp 1866-1871, 2003).

The fact that the samples with the least thermal treatment show the highest $CO_2$ content (due to the peak heights) and the sample with the longest treatment show the least $CO_2$ content is not in contradiction with previous observations. Even though more $CO_2$ is generated with respect to an increase in temperature (as suggested by Shi et al), less of the gas is trapped in the hydroxyapatite lattice with the longer thermal treatments as opposed to shorter thermal treatments. This FTIR semi-quantitative study proves that the heating times employed for the current invention results in $CO_2$ contents between that of the unsintered material and U.S. Pat. No. 5,167,961 material. This further substantiates that the heating times employed of the current invention are significantly shorter than that of the prior art.

The invention claimed is:

1. A sintered hydroxyapatite material derived from natural bone material, the hydroxyapatite material having a specific surface area greater than 80 $m^2$/gram after sintering and a residual protein content of greater than 150 ppm and not more than 1800 ppm;
wherein residual protein is protein remaining from the natural bone.

2. The hydroxyapatite material according to claim 1, wherein the hydroxyapatite material has a specific surface area of at least 90 $m^2$/g.

3. The hydroxyapatite material according to claim 1, wherein the hydroxyapatite material has a specific surface area of greater than 100 $m^2$/g.

4. A medical device comprising sintered hydroxyapatite material derived from natural bone material, the hydroxyapatite material having a surface area greater than 80 $m^2$/gram after sintering and a residual protein content of greater than 150 ppm and not more than 1800 ppm;
   wherein residual protein is protein remaining from the natural bone.

5. A medical device according to claim 4 further comprising a low surface area biphasic calcium phosphate (HA/TCP) component having a surface area of less than 30 m²/gram.

6. A medical device according to claim 5 wherein the sintered hydroxyapatite material and/or the low surface area biphasic calcium phosphate are combined with a bioresorbable carrier gel or polymer that can be injected.

* * * * *